United States Patent
Kajihara et al.

(10) Patent No.: US 11,214,592 B2
(45) Date of Patent: Jan. 4, 2022

(54) PRODUCTION METHOD FOR AMINO-ACID POLYMER

(71) Applicant: Glytech, Inc., Kyoto (JP)

(72) Inventors: Yasuhiro Kajihara, Osaka (JP); Masayuki Izumi, Osaka (JP); Ryo Okamoto, Osaka (JP); Takuya Haraguchi, Osaka (JP); Takefumi Murase, Kyoto (JP)

(73) Assignee: Glytech, Inc., Kyoto (JP)

( * ) Notice: Subject to any disclaimer, the term of this patent is extended or adjusted under 35 U.S.C. 154(b) by 252 days.

(21) Appl. No.: 16/489,950

(22) PCT Filed: Feb. 28, 2018

(86) PCT No.: PCT/JP2018/007647
§ 371 (c)(1),
(2) Date: Aug. 29, 2019

(87) PCT Pub. No.: WO2018/159721
PCT Pub. Date: Sep. 7, 2018

(65) Prior Publication Data
US 2021/0284682 A1    Sep. 16, 2021

(30) Foreign Application Priority Data
Mar. 2, 2017  (JP) .............................. JP2017-039354

(51) Int. Cl.
| | | |
|---|---|---|
| *C07K 1/00* | (2006.01) | |
| *C07K 1/02* | (2006.01) | |
| *C40B 40/10* | (2006.01) | |
| *C07K 1/06* | (2006.01) | |
| *C08G 69/10* | (2006.01) | |

(52) U.S. Cl.
CPC ................ *C07K 1/026* (2013.01); *C07K 1/06* (2013.01); *C08G 69/10* (2013.01); *C40B 40/10* (2013.01)

(58) Field of Classification Search
None
See application file for complete search history.

(56) References Cited

U.S. PATENT DOCUMENTS 9,243,028 B2    1/2016  Xian et al.

FOREIGN PATENT DOCUMENTS

| WO | 1996034878 | 11/1996 |
| WO | 1998028434 | 7/1998 |
| WO | 1998056807 | 12/1998 |

OTHER PUBLICATIONS

Haraguchi et al. "Prebiotic peptide bond formation by alpha-amino thioacid" The Chemical Society of Japan, 1 C3-56 (1 page) (2017).
Liu et al. "Oxidative acylation using thioacids" Letters to Nature, 389:52-54 (1997).
Luger et al. "Crystal structure of the nucleosome core particle at 2.8 A resolution" Nature, 389(6648):251-260 (1997).
Mali et al. "Thioacetic acid/NaSH-mediated synthesis of N-protected amino thioacids and their utility in peptide synthesis" Journal of Organic Chemistry, 79(6):2377-2383 (2014).
Pan et al. "Facile Amide Formation via S-Nitrosothioacids" Organic Letters, 13(5):1092-1094 (2011).
Shangguan et al. "The Reaction of Thio Acids with Azides: A New Mechanism and New Synthetic Applications" Journal of the American Chemical Society, 125(26):7754-7755 (2003).
Sumikawa et al. "Application of Peptide Thioacids to NCL-type Sequential Condensation of Peptide Fragments" Peptide Science, 2008:175-176 (2009).
Wang et al. "Promising General Solution to the Problem of Ligating Peptides and Glycopeptides" Journal of the American Chemical Society, 132(47):17045-17051 (2010).
Extended European Search Report corresponding to European Patent Application No. 18761801.2 (9 pages) (dated Dec. 7, 2020).

*Primary Examiner* — Jeanette M Lieb
(74) *Attorney, Agent, or Firm* — Myers Bigel, P.A.

(57) ABSTRACT

The object of the present invention is to provide a method for manufacturing an amino acid polymer more simply and efficiently compared to conventional methods for manufacturing amino acid polymers.

The present invention provides a method for manufacturing an amino acid polymer with thioacid amino acids. Specifically, the manufacturing method of the present invention comprises (A) a step of preparing first and second thioacid amino acids, (B) a step of subjecting said first and second thioacid amino acids to an oxidation reaction to obtain an amino acid polymer linked by peptide bonds. The manufacturing method of the present invention is characterized in that it partially uses thioacid amino acids that do not possess a protecting group.

24 Claims, 9 Drawing Sheets

[CHEMICAL FORMULA 2]

FIRST REACTION

COMPOUND (7)

SECOND REACTION

COMPOUND (8)

AA REPRESENTS ONE MOLECULE OF AMINO ACID

[Figure 11]

[CHEMICAL FORMULA 3]

COMPOUND (8)

AA REPRESENTS ONE MOLECULE OF AMINO ACID

PRODUCTION METHOD FOR AMINO-ACID POLYMER

TECHNICAL FIELD

The present invention relates to a method for manufacturing an amino acid polymer, in particular to a method for manufacturing a polymer of amino acids linked by peptide bonds with thioacid amino acids.

BACKGROUND ART

Amino acid polymers are utilized for various purposes such as many industrial products, additives to these products, as well as synthetic intermediates of compounds contained in these products. For example, polyaspartic acid which is a homopolymer of aspartic acid is used as detergents, fertilizers, agrochemicals, cosmetics, or additives to these products. Moreover, in recent years, polyalanine contained in spider's thread has gathered attention in regards to its strength. In this way, various use has been found for amino acid polymers as functional high molecular materials that render new characteristics which were not conventionally possessed, and it is anticipated that there will be increasing needs for industrially manufacturing amino acid polymers in years to come.

Various methods such as biological and chemical approaches have been developed as methods for manufacturing amino acid polymers, although room for improvement is recognized in various points such as manufacturing efficiency and quality.

For example, for biological approach, this includes e.g. the restriction for introducing non-natural type amino acids, or the ununiformity of sugar chain structure in glycoproteins.

Moreover, for chemical approach, as opposed to biological approach, freedom of design and structural control are allowed, but steps of protection and deprotection during synthesis are required. For this reason, side reactions that occur during those steps, as well as restriction to productivity such as cost and time are pointed out as problems. It is also pointed out as a problem that the use of toxins with high toxicity is often times necessary in the deprotection step.

Accordingly, in order to improve the productivity of chemical synthesis that allows freedom of design and structural control, it is desired to improve the protection and deprotection steps to simpler and more rapid as well as safer steps.

Thioacid is a generic term for compounds having a thioacid group (—COSH). Methods for forming amide bonds with thioacid thus far known are coupling with an amino acid having an azide group (Non-Patent Literature 1), a method of utilizing thioacid S—S dimer as active ester (Non-Patent Literature 2), and a method of activating by nitrosation of thioacid (Non-Patent Literature 3).

Moreover, methods known for forming peptide bonds using thioacid amino acid are a method of using protected thioacid amino acid S—S dimer as active ester (Non-Patent Literature 4), and a method of utilizing thioacid amino acid as HOBt ester precursor (Non-Patent Literature 5).

CITATION LIST

[Non-Patent Literature 1] J. Am. Chem. Soc. 2003, 125, 7754-7755
[Non-Patent Literature 2] Nature, Vol 389, 4 Sep. 1997
[Non-Patent Literature 3] Org. Lett., Vol. 13, No. 5, 2011
[Non-Patent Literature 4] J. Org. Chem. 2014, 79, 2377-2383
[Non-Patent Literature 5] J. Am. Chem. Soc. 9Vol. 132, No. 47, 2010

SUMMARY OF THE INVENTION

Problems to be Solved by the Invention

The object of the present invention is to provide a method for manufacturing an amino acid polymer more simply and efficiently compared to conventional methods for manufacturing amino acid polymers.

Means for Solving the Problems

Peptide bonds between amino acids are formed by using the α-amino group of one amino acid as the nucleophilic group to allow condensation with the carboxyl group of the other amino acid. Since the carboxyl group activated during condensation will become more likely to react with α-amino groups as well as various functional groups having nucleophilicity present in the side chain, it is necessary to protect the side chains and α-amino groups (those other than the subject of reaction) of amino acids in order to manufacture a polymer of structurally controlled amino acids.

As a result of repeated extensive investigation by the present inventors in order to solve the problems of the present invention, it was surprisingly found that an amino acid polymer linked by peptide bonds can be efficiently manufactured without protecting α-amino groups and side chains when thioacid amino acid is employed for the manufacturing of an amino acid polymer and subjecting them to an oxidation reaction with each other. The present inventors further surprisingly found that an amino acid polymer can be similarly manufactured even when using lysine which possess a functional group having a long side chain and nucleophilicity and thus thought that protection was requisite in conventional amino acid condensation methods. This means that the manufacturing method of the present invention can be used for various purposes without being restricted by the type of amino acid side chain.

The present invention is based on the above knowledge, and encompasses the following characteristics:
[1] A method for manufacturing a polymer of amino acids linked by peptide bonds, characterized in that it comprises:
(A) a step of preparing first and second amino acid derivatives each shown below:

$$H_2N—CH(R)—COSH \qquad (1)$$

(wherein R represents the side chain of any amino acid); and
(B) a step of subjecting said first amino acid derivative and second amino acid derivative to an oxidation reaction to obtain the compound shown below:

$$H_2N—CH(R)—CO—HN—CH(R)—CO—SH \qquad (2)$$

(wherein each R, each independently, represents the side chain of any amino acid);
where at least one of said first amino acid derivative and second amino acid derivative does not possess a protecting group.
[2] The method according to manufacturing method [1], wherein said first amino acid derivative and second amino acid derivative both do not possess a protecting group.
[3] The manufacturing method according to [1] or [2], comprising:

(C) a step of subjecting Compound (2) obtained in step (B) to an oxidation reaction with a third amino acid derivative shown below:

(1)

(wherein R represents the side chain of any amino acid) to obtain the compound shown below:

(3)

(wherein each R, each independently, represents the side chain of any amino acid).

[4] The manufacturing method according to [3], characterized in carrying out step (C) multiple times to obtain the compound shown below:

(4)

(wherein each R, each independently, represents the side chain of any amino acid, and n represents in integer that is 2 or more).

[5] The manufacturing method according to [3] or [4], wherein said one or more third amino acid derivative(s) does not possess a protecting group.

[6] The manufacturing method according to any of [1] to [5], further comprising:

(D) a step of reacting Compound (2) obtained in step (B), or Compound (3) or Compound (4) obtained in step (C), with a nucleophilicity reagent shown below:

H—X (5)

(wherein X represents a substituent bound via an atom selected from the group consisting of N, O, S, and Se) to obtain the compound shown below:

(6)

(wherein each R, each independently, represents the side chain of any amino acid, m represents any integer, and X represents a substituent bound via an atom selected from the group consisting of N, O, S, and Se).

[7] The manufacturing method according to [6], wherein X is a substituent bound via an N atom or S atom.

[8] The manufacturing method according to [4], which is a method for manufacturing a polymer comprising 4 to 20 amino acids.

[9] The manufacturing method according to any of [1] to [8], wherein the first or second amino acid derivative, or at least one of said more than one third amino acid derivatives has an unprotected 4-aminobutyl group as a side chain.

[10] The manufacturing method according to any of [1] to [8], wherein the side chains of said first and second amino acid derivatives, and of said one or more third amino acid derivative are identical.

[11] The manufacturing method according to [10], wherein said side chains are all methyl groups.

[12] A method for manufacturing a polymer of more than one amino acids linked by peptide bonds, characterized in that it comprises:

(a) a step of preparing more than one amino acid derivatives shown below:

(1)

(wherein R represents the side chain of any amino acid);

(b) a step of subjecting said more than one amino acid derivatives to an oxidation reaction to obtain more than one compound shown below:

(7)

(wherein each R, each independently, represents the side chain of any amino acid, x represents any integer)

and/or the compound shown below:

(8)

(wherein each R, each independently, represents the side chain of any amino acid, and y and z represent any integer), where a portion or all of said more than one amino acid derivatives do not possess a protecting group.

[13] The method according to [12], wherein all of said more than one amino acid derivatives do not possess a protecting group.

[14] The method according to [12] or [13], wherein the compound obtained in step (b) comprises Compound (7).

[15] The manufacturing method according to [14], further comprising:

(c1) a step of reacting Compound (7) obtained in step (b) with a nucleophilicity reagent shown below:

H—X (5)

(wherein X represents a substituent bound by an atom selected from the group consisting of N, O, S, and Se) to obtain the compound shown below:

(9)

(wherein each R, each independently, represents the side chain of any amino acid, x represents any integer, and X represents a substituent bound by an atom selected from the group consisting of N, O, S, and Se).

[16] The manufacturing method according to [15], wherein X is a substituent bound by an N atom or S atom.

[17] The manufacturing method according to [12] or [13], wherein the compound obtained in step (b) comprises Compound (8).

[18] The manufacturing method according to [17], further comprising:

(c2) a step of reacting Compound (8) obtained in step (b) with a nucleophilicity reagent shown below:

H—X (5)

(wherein X represents a substituent bound by an atom selected from the group consisting of N, O, S, and Se) to obtain the compound shown below:

(10)

(wherein each R, each independently, represents the side chain of any amino acid, y represents any integer, and X represents a substituent bound by an atom selected from the group consisting of N, O, S, and Se) and below:

(11)

(wherein each R, each independently, represents the side chain of any amino acid, z represents any integer, and X represents a substituent bound by an atom selected from the group consisting of N, O, S, and Se).

[19] The manufacturing method according to [18], wherein X is a substituent bound by an N atom or S atom.

[20] The manufacturing method according to any of [12] to [19], which is a method for manufacturing a polymer comprising 4 to 20 amino acids.

[21] The manufacturing method according to any of [12] to [20], wherein at least one of said more than one amino acid derivatives has an unprotected 4-aminobutyl group as a side chain.

[22] The manufacturing method according to any of [12] to [21], wherein the side chains of said more than one amino acid derivatives are identical.

[23] The manufacturing method according to [22], wherein said side chains are all methyl groups.

[24] The manufacturing method according to any of [12] to [23] which is for producing a polypeptide library.

Those skilled in the art shall recognize that an invention of any combination of one or more characteristics of the present invention described above is encompassed by the scope of the present invention.

Effects of the Invention

According to the manufacturing method of the present invention, amino acid polymers can be manufactured extremely efficiently compared to conventional methods of utilizing a protecting group.

Moreover, since there is no need to utilize a protecting group in the manufacturing method of the present invention, problems involved with conventional methods that use highly toxic toxins for deprotection can be easily avoided.

Since the manufacturing method of the present invention allows synthesis of large amounts of more than one amino acid polymers, it may be suitable for industrial production of polyamino acids or production of a polypeptide library.

DESCRIPTION OF EMBODIMENTS

An "amino acid" herein is employed in its broadest meaning, and comprises natural amino acids, i.e., serine (Ser), asparagine (Asn), valine (Val), leucine (Leu), isoleucine (Ile), alanine (Ala), tyrosine (Tyr), glycine (Gly), lysine (Lys), arginine (Arg), histidine (His), aspartic acid (Asp), glutamic acid (Glu), glutamine (Gln), threonine (Thr), cysteine (Cys), methionine (Met), phenylalanine (Phe), tryptophan (Trp), and proline (Pro), as well as non-natural amino acids such as amino acid variants. Accordingly, amino acids herein include, for example, L-amino acids; D-amino acids; chemically modified amino acids; amino acids which will not be materials for configuring proteins in vivo such as norleucine, β-alanine, and ornithine; variants where the amino acid side chain substituent is substitute with yet another substituent, and the like.

An "amino acid derivative" herein refers to an amino acid having the carboxyl group of the amino acid converted into a thioacid group (—COSH) (also referred to herein as a "thioacid amino acid"), typically those having an α-amino group and the structure below:

$$H_2N-CH(R)-COSH \quad (1)$$

R in Compound (1) represents the side chain of any amino acid, and accordingly, R may be the side chain of a natural amino acid or may be those having been substituted with a non-natural side chain.

Various methods are known for the method of introducing a thioacid group into the carboxyl group. For example, such methods include a method for manufacturing in the presence of an antimony catalyst (such as $Ph_3SbO$) by a reaction between a carboxylic acid corresponding to the target thiocarboxylic acids and phosphorus sulfide (Chem. Ber, 123, 2081-2082(1990)), a method of employing hydrogen sulfide as the sulfidizing agent (J. Org. Chem., 25, 180-182(1960)), a method of converting a carboxylic acid into an acid halide, and then reacting with a metal salt of hydrogen sulfide (sodium or potassium salt) (Org. Synth., 4, 924(1963); Synthesis, 998-1004(2005)), a method of employing N,N-dimethylformthioamide or thioacetamide as the sulfidizing agent on an acid halide (Phosphorus, Sulfur, and Silicon, 178, 1661-1665(2003)), converting into a mixed acid anhydride by reaction between a chlorocarbonic acid ester and a corresponding carboxylic acid, and then reacting with hydrogen sulfide (Chem. Pharm. Bull., 34, 999-1014 (1986)), and the like. In the present invention, amino acids are converted into thioacid amino acids with these known methods and employed for the present invention. Alternatively, amino acid derivatives can be prepared for example by conversion of the carboxyl group in the amino acid to a thioester group and deprotection of the protecting group of sulfur atom.

In one aspect, the present invention relates to a method for manufacturing a polymer of amino acids linked by peptide bonds.

Without being constrained to a particular theory, in the manufacturing method of the present invention, formation of peptide bonds is thought to proceed by formation of disulfide (S—S) bonds between amino acid derivatives, followed by intramolecular transfer reaction (see below).

[Chemical Formula 1]

Accordingly, in the manufacturing method of the present invention, any method and condition where disulfide bonds are formed between thioacid amino acids can be adopted in order to proceed the reaction. Such methods and conditions are known to those skilled in the art, and those skilled in the art can suitably select appropriate methods and conditions by referring to e.g. CHEMICAL APPROACHES to the SYNTHESIS of PEPTIDES and PROTEIN Chapter 5 Formation of Disulfide Bridge pp. 209-236, 1997, CRC PRESS.

The manufacturing method of the present invention, in particular the above reaction can be proceeded by an oxidation reaction.

Accordingly, in one aspect, the manufacturing method of the present invention is characterized in that it comprises:

(A) a step of preparing first and second amino acid derivatives each shown below:

$$H_2N\text{—}CH(R)\text{—}COSH \qquad (1)$$

(wherein R represents the side chain of any amino acid); and (B) a step of subjecting said first amino acid derivative and second amino acid derivative to an oxidation reaction to obtain the compound shown below:

$$H_2N\text{—}CH(R)\text{—}CO\text{—}HN\text{—}CH(R)\text{—}CO\text{—}SH \qquad (2)$$

(wherein each R, each independently, represents the side chain of any amino acid)
where at least one of said first amino acid derivative and second amino acid derivative does not possess a protecting group.

"At least one of first amino acid derivative and second amino acid derivative does not possess a protecting group" herein means that at least one of first amino acid derivative and second amino acid derivative does not possess any protecting group on its side chain or functional group.

A protecting group herein means a protecting group commonly used for protecting side chains and amino groups in amino acid polymer synthesis, and can include, but is not limited to, for example, as the protecting group for a hydroxyl group, e.g. a methyl group, a tert-butyl group, a benzyl group, a benzoyl group, an acetyl (Ac) group, a trimethylsilyl (TMS) group, a triethylsilyl (TES) group, a tert-butyldimethylsilyl (TBS or TBDMS) group, and the like. The protecting group for an amino group can include, for example, as lipophilic protecting groups, carbonate-based or amide-based protecting groups such as 9-fluorenylmethoxycarbonyl (Fmoc) group, t-butyloxycarbonyl (Boc) group, a benzyl group, a allyloxycarbonyl (Alloc) group, 2,2,2-trichloroethoxycarbonyl (troc) group, allyloxycarbonyl group, acetyl group, and the like.

In the manufacturing method of the present invention, as described above, although at least one of first amino acid derivative or second amino acid derivative does not possess a protecting group, it is not precluded that the other amino acid derivative possesses a protecting group. Accordingly, both cases of when using a first amino acid derivative that possesses a protecting group and a second amino acid derivative that does not possess a protecting group, and when using a first amino acid derivative that does not possess a protecting group and a second amino acid derivative that possesses a protecting group are within the scope of the present invention. Preferably, amino acid derivatives that do not possess a protecting group are used as both the first amino acid derivative and the second amino acid derivative.

In the manufacturing method of the present invention, the oxidation reaction can be performed by, but is not limited to, oxidation by use of an oxidant, and the like.

An oxidant that can be used in the present invention is not particularly limited, as long as it is an oxidant that can form disulfide bonds by oxidative coupling of sulfanyl groups (SH) in thioacid groups (—COSH). Examples of such an oxidant can include, but is not limited to, iron chloride (III), iodine, and the like. In one embodiment of the present invention, oxidation reaction is carried out by use of an oxidant, e.g. iron chloride (III).

In the present invention, the oxidation reaction can be performed with water alone or with a mixed solvent of water and an organic solvent. Organic solvents that can be employed are, but not limited to, aliphatic hydrocarbon solvents such as hexane or cyclohexane, aromatic hydrocarbon solvents such as benzene or toluene, halogen-containing solvents such as dichloromethane or chloroform, aprotic polar solvents such as ethyl acetate or acetonitrile, and protic polar solvents such as ethanol or methanol.

In the present invention, the reaction temperature in the oxidation reaction is not particularly limited, and the reaction can be performed at e.g. room temperature. The pH condition for the oxidation reaction is also not particularly limited, and can be in the range of e.g. pH 1-4.

In the manufacturing method of the present invention, depending on the amino acid polymer to be the target for manufacture, the side chains of the first and second amino acid derivatives may be identical or different side chains.

The manufacturing method of the present invention can further comprise (C) a step of subjecting the above Compound (2) obtained in step (B) to an oxidation reaction with a third amino acid derivative shown below:

$$H_2N\text{—}CH(R)\text{—}COSH \qquad (1)$$

(wherein R represents the side chain of any amino acid) to obtain the compound shown below:

$$H_2N\text{—}CH(R)\text{—}CO\text{—}(HN\text{—}CH(R)\text{—}CO)_2\text{—}SH \qquad (3)$$

(wherein each R, each independently, represents the side chain of any amino acid).

By step (C), one additional molecule of amino acid is linked by peptide bond to Compound (2).

The third amino acid derivative may or may not possess a protecting group. In the preferred embodiment of the present invention, the third amino acid derivative does not possess a protecting group. Moreover, depending on the type of amino acid polymer to be the target for manufacture, the side chain of the third amino acid derivative may have a side chain identical to one or both of the first and second amino acid derivatives, or may be different from both.

In the manufacturing method of the present invention, step (C) can be repeated multiple times as necessary to obtain the compound shown below having the desired length:

$$H_2N\text{—}CH(R)\text{—}CO\text{—}(HN\text{—}CH(R)\text{—}CO)_n\text{—}SH \qquad (4)$$

(wherein each R, each independently, represents the side chain of any amino acid, and n represents in integer that is 2 or more).

In this way, an amino acid polymer of desired length having controlled sequence can be efficiently manufactured.

Accordingly, in the manufacturing method of the present invention, potentially, more than one third amino acid derivatives may be used. The more than one third amino acid derivatives used, each independently, may or may not possess a protecting group. In a preferred embodiment, all of the one or more third amino acid derivative used do not possess a protecting group. Moreover, depending on the type of amino acid polymer to be the target for manufacture, the side chain of the more than one third amino acid derivatives used, each independently, may have a side chain identical to one or both of the first and second amino acid derivatives, or may be different from both.

In one embodiment, the manufacturing method of the present invention can further comprise a step of derivatizing the amino acid polymer obtained. Specifically, the manufacturing method of the present invention can further comprise:

(D) a step of reacting Compound (2) obtained in step (B), or Compound (3) or Compound (4) obtained in step (C), with a nucleophilicity reagent shown below:

H—X   (5)

(wherein X represents a substituent bound by an atom selected from the group consisting of N, O, S, and Se) to obtain the compound shown below:

H$_2$N—CH(R)—CO—(HN—CH(R)—CO)$_m$—X   (6)

(wherein each R, each independently, represents the side chain of any amino acid, m represents any integer, and X represents a substituent bound by an atom selected from the group consisting of N, O, S, and Se).

In this way, the amino acid polymer obtained in the form of an SH body can be converted into a desired form.

Step (D) may be performed in a like manner to amino acid or peptide derivatizing methods well-known to those skilled in the art. For example, amide-based solvents, aliphatic hydrocarbon solvents such as hexane, or cyclohexane, aromatic hydrocarbon solvents such as benzene or toluene, halogen-containing solvents such as dichloromethane or chloroform, aprotic polar solvents such as ethyl acetate or acetonitrile, and protic polar solvents such as ethanol or methanol or water can be employed for the reaction between Compound (2) or (3) and nucleophilicity reagent (5). This reaction is in particular performed in an acidic to neutral buffer solution. Examples of the buffer solution include phosphate buffer, Tris buffer solution, HEPES buffer solution, citric acid buffer solution, and the like. These buffer solutions may be used alone or in a mixture of two or more.

The reaction temperature of step (D) is not particularly limited, and can be carried out at a range of 0° C.-30° C., preferably carried out at a range of 0° C.-20° C., and further preferably carried out at a range of 0° C.-10° C. Further, the reaction time is not particularly limited, and can be carried out at a range of 1 minute-5 hours, preferably carried out at a range of 1 minute-2 hours, and further preferably carried out at a range of 1 minute-30 minutes. Moreover, the pH condition of step (D) is not particularly limited, and can be carried out at a range of 1-8, preferably carried out at a range of 2-7, and further preferably carried out at a range of 4-7.

Specific examples of Compound (5) can include water, alkyl alcohols such as methanol, aryl alcohols such as benzyl alcohol, protected or unprotected hydrazine, alkylthiols such as ethanthiol, aryl thiols such as benzylthiol, selenocompounds, and the like.

In one embodiment, X in Compound (5) is a substituent bound by an N atom or S atom, and accordingly the amino acid polymer is obtained as a hydrazide body or in the form of a thioester, respectively.

In another aspect, the present invention relates to a method for manufacturing a polymer of more than one amino acids linked by peptide bonds, wherein the said method comprises (a) a step of preparing more than one amino acid derivatives shown below:

H$_2$N—CH(R)—COSH   (1)

(wherein R represents the side chain of any amino acid); and
(b) a step of subjecting said more than one amino acid derivatives to an oxidation reaction to obtain more than one compound shown below:

H$_2$N—CH(R)—CO—(HN—CH(R)—CO)$_x$—SH   (7)

(wherein each R, each independently, represents the side chain of any amino acid, x represents any integer) and/or the compound shown below:

H$_2$N—CH(R)—CO—(HN—CH(R)—CO)$_y$—S—S—
(CO—CH(R)—NH)$_z$—CO—CH(R)—NH$_2$   (8)

(wherein each R, each independently, represents the side chain of any amino acid, and y and z represent any integer).

In this aspect, the manufacturing method of the present invention can be characterized in that it subjects more than one amino acid derivatives simultaneously to an oxidation reaction. Further, in this aspect, the manufacturing method of the present invention is characterized in that at least a portion or all of said more than one amino acid derivatives do not possess a protecting group.

In the manufacturing method of the present invention, "a portion of said more than one amino acid derivatives does not possess a protecting group" means that the more than one amino acid derivatives prepared in step (a) comprise an amino acid derivative that does not possess a protecting group, and the proportion of the amino acid derivatives that do not possess a protecting group is not necessarily an issue, although it is preferred that preferably at least 50%, more preferably at least 60%, more preferably at least 70%, more preferably at least 80%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, and more preferably at least 99% of the more than one amino acid derivatives are amino acid derivatives that do not possess a protecting group. In the present invention, preferably, all of the more than one amino acid derivatives prepared in step (a) do not possess a protecting group.

Figure 10:
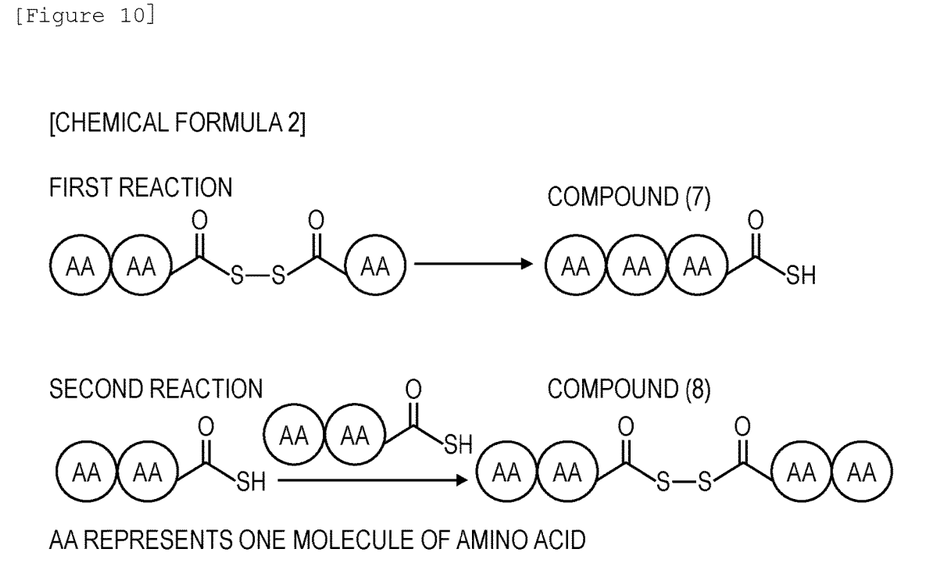
FIG. 10 illustrates the sequential processes of subjecting more than one amino acid derivatives simultaneously to an oxidation reaction.

Step (b) is a step of subjecting the more than one amino acid derivatives prepared in step (a) simultaneously to an oxidation reaction. Without being constrained to a particular theory, it is thought that when subjecting more than one amino acid derivatives simultaneously to an oxidation reaction, the monomer or polymer of the amino acid derivative and the monomer of the amino acid derivative produce sequential processes of the formation of disulfide bond and intramolecular metastasis, namely a first reaction of forming a peptide bond and a second reaction of forming a disulfide bond between the amino acid derivative polymers (FIG. 10).

Figure 11:
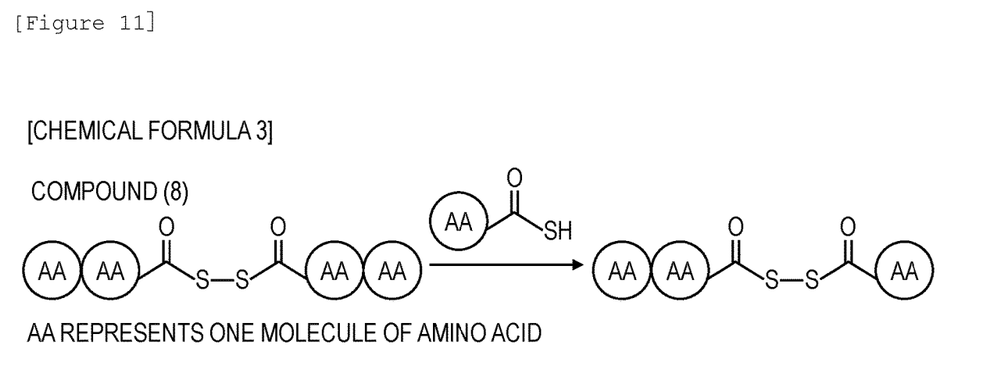
FIG. 11 illustrates an exchange reaction forming an (amino acid polymer)-S—S-(amino acid monomer) from Compound (8).

Moreover, without being constrained to a particular theory, it is thought that when (amino acid polymer)-S—S-(amino acid polymer) (Compound (8)) is produced by the second reaction, intramolecular metastasis does not occur in this molecule, but when the amino acid derivative monomer is present in the reaction system, one of the amino acid polymers that is present via a disulfide bond and the said amino acid derivative monomer have an exchange reaction to form (amino acid polymer)-S—S-(amino acid monomer)

(see below), and extension of amino acids occurs due to this molecule producing intramolecular transfer reaction (FIG. 11).

Incidentally, it is thought that when such an exchange reaction with the amino acid derivative monomer does not occur, amino acid polymers form a disulfide bond with each other, after which point further extension of amino acids no longer occurs, and therefore long-chain amino acid polymers cannot be manufactured. It can also be speculated and confirmed from the Examples herein where a polymer having a length of a maximum of 19 amino acids could be manufactured, that the probability of the exchange reaction with the amino acid derivative monomer occurring is high.

On the other hand, it is thought that when no available amino acid derivative monomer is present at the time when (amino acid polymer)-S—S-(amino acid polymer) is produced, the exchange reaction with the amino acid derivative monomer will not occur, and therefore further extension does not occur. Although the manufacturing method of the present invention may optionally further comprise a step of adding the amino acid derivative monomer to the reaction system to proceed further reaction, in any case, it shall be recognized by those skilled in the art that upon performing step (b), Compound (8) may potentially be produced in addition to Compound (7).

Moreover, in the manufacturing method of the present invention, depending on the amino acid polymer to be the subject of manufacture, the side chains of said "more than one amino acid derivatives" may be all identical or may be different. For example, by having all identical side chains of said "more than one amino acid derivatives", the manufacturing method of the present invention may become one that is suitable for the objective of obtaining a larger amount of a particular polyamino acid. Such a polyamino acid can include, for example but is not limited to, polyalanine. Polyalanine can be prepared by preparing a uniform collection consisting of amino acid derivatives having a methyl group as the side chain, as said "more than one amino acid derivatives", and then subjecting this to an oxidation reaction. Further, by preparing and employing said "more than one amino acid derivatives" so that they comprise the side chains of the 20 types of natural amino acids, the manufacturing method of the present invention may become one that is suitable for the object of obtaining a polypeptide library.

In one embodiment, the manufacturing method of the present invention can further comprise:
(c1) a step of reacting Compound (7) obtained in step (b) with a nucleophilicity reagent shown below:

(wherein X represents a substituent bound by an atom selected from the group consisting of N, O, S, and Se)
to obtain the compound shown below:

(wherein each R, each independently, represents the side chain of any amino acid, x represents any integer, and X represents a substituent bound by an atom selected from the group consisting of N, O, S, and Se).

In this way, the amino acid polymer obtained in the form of an SH body can be converted into a desired form.

step (c1) may be performed in a like manner to amino acid or peptide derivatizing methods well-known to those skilled in the art. Amide-based solvents, aliphatic hydrocarbon solvents such as hexane, or cyclohexane, aromatic hydrocarbon solvents such as benzene or toluene, halogen-containing solvents such as dichloromethane or chloroform, aprotic polar solvents such as ethyl acetate or acetonitrile, and protic polar solvents such as ethanol or methanol or water can be employed for the reaction between Compound (7) and nucleophilicity reagent (5). This reaction is in particular performed in an acidic to neutral buffer solution. Examples of the buffer solution include phosphate buffer, Tris buffer solution, HEPES buffer solution, citric acid buffer solution, and the like. These buffer solutions may be used alone or in a mixture of two or more.

The reaction temperature of step (c1) is not particularly limited, and can be carried out at a range of 0° C.-30° C., preferably carried out at a range of 0° C.-20° C., and further preferably carried out at a range of 0° C.-10° C. Further, the reaction time is not particularly limited, and can be carried out at a range of 1 minute-5 hours, preferably carried out at a range of 1 minute-2 hours, and further preferably carried out at a range of 1 minute-30 minutes. Moreover, the pH condition of step (c1) is not particularly limited, and can be carried out at a range of 1-8, preferably carried out at a range of 2-7, and further preferably carried out at a range of 4-7.

Specific examples of Compound (5) can include water, alkyl alcohols such as methanol, aryl alcohols such as benzyl alcohol, protected or unprotected hydrazine, alkylthiols such as ethanthiol, aryl thiols such as benzylthiol, and selenocompounds.

In one embodiment, X in Compound (5) is a substituent bound by an N atom or S atom, and accordingly the amino acid polymer is obtained in as a hydrazide body or in the form of a thioester, respectively.

In another embodiment, the manufacturing method of the present invention can further comprise:
(c2) a step of reacting Compound (8) obtained in step (b) with a nucleophilicity reagent shown below:

(wherein X represents a substituent bound by an atom selected from the group consisting of N, O, S, and Se)
to obtain the compound shown below:

(wherein each R, each independently, represents the side chain of any amino acid, y represents any integer, and X represents a substituent bound by an atom selected from the group consisting of N, O, S, and Se)
and below:

(wherein each R, each independently, represents the side chain of any amino acid, z represents any integer, and X represents a substituent bound by an atom selected from the group consisting of N, O, S, and Se).

Step (c2) is a step of obtaining Compounds (10) and (11) in derivatized forms from one molecule of Compound (8) by cleaving disulfide bonds by using Compound (4) which is a nucleophilicity reagent.

Cleaving of a disulfide bond by a nucleophilicity reagent is known to those skilled in the art, such as hydrolysis by water, esterification by alcohol, amidation by amino compounds, hydrazidation, thioesterification by thiols, and seleno esterification by selenocompounds. Amide-based solvents, aliphatic hydrocarbon solvents such as hexane, or cyclohexane, aromatic hydrocarbon solvents such as benzene or toluene, halogen-containing solvents such as dichloromethane or chloroform, aprotic polar solvents such as ethyl acetate or acetonitrile, and protic polar solvents such as ethanol or methanol or water can be employed for the reaction between Compound (8) and nucleophilicity reagent (5). This reaction is in particular performed in an acidic to neutral buffer solution. Examples of the buffer solution include phosphate buffer, Tris buffer solution, HEPES buffer solution, citric acid buffer solution, and the like. These buffer solutions may be used alone or in a mixture of two or more.

The reaction temperature of step (c2) is not particularly limited, and can be carried out at a range of 0° C.-30° C., preferably carried out at a range of 0° C.-20° C., and further preferably carried out at a range of 0° C.-10° C. Further, the reaction time is not particularly limited, and can be carried out at a range of 1 minute-5 hours, preferably carried out at a range of 1 minute-2 hours, and further preferably carried out at a range of 1 minute-30 minutes. Moreover, the pH condition of step (c2) is not particularly limited, and can be carried out at a range of 1-8, preferably carried out at a range of 2-7, and further preferably carried out at a range of 4-7.

Specific examples of Compound (5) can include water, alkyl alcohols such as methanol, aryl alcohols such as benzyl alcohol, protected or unprotected hydrazine, alkylthiols such as ethanthiol, aryl thiols such as benzylthiol, and selenocompounds.

According to the manufacturing method of the present invention, for example a polymer or a collection of polymers comprising 4-20, 5-20, 6-20, 7-20, 8-20, 9-20, or 10-20 amino acids can be efficiently manufactured.

Moreover, since the manufacturing method of the present invention allows manufacture of an amino acid polymer linked by peptide bonds even when an amino acid derivative that possesses a highly reactive side chain such as lysine, which possesses a 4-aminobutyl group as the side chain and has been said to require protection in conventional amino acid condensation reactions, is employed unprotected, it has the advantages of not being constrained by the type of amino acid and having extremely high versatility.

Note that the terms used herein are to be employed to describe particular embodiments, and do not intend to limit the invention.

Moreover, the term "comprising" as used herein, unless the content clearly indicates to be understood otherwise, intends the presence of the described items (such as components, steps, elements, and numbers), and does not exclude the presence of other items (such as components, steps, elements, and numbers).

Unless otherwise defined, all terms used herein (including technical and scientific terms) have the same meanings as those broadly recognized by those skilled in the art of the technology to which the present invention belongs. The terms used herein, unless explicitly defined otherwise, are to be construed as having meanings consistent with the meanings herein and in related technical fields, and shall not be construed as having idealized or excessively formal meanings.

Terms such as first and second are sometimes employed to express various elements, and it should be recognized that these elements are not to be limited by these terms. These terms are employed solely for the purpose of discriminating one element from another, and it is for example possible to describe a first element as a second element, and similarly, to describe a second element as a first element without departing from the scope of the present invention.

The present invention will now be more specifically described by Examples. However, the present invention can be embodied by various embodiments, and shall not be construed as being limited to the Examples described herein.

EXAMPLES

Raw Materials

In the Examples below, the following substances were used: N,N-diisopropylethylamine (DIPEA), Trifluoroacetic acid (TFA), triisopropylsilane (TIPS), N,N-dimethyl-4-aminopyridine (DMAP), Dichloromethane (DCM), formic acid (FA), Acetonitrile (MeCN), (benzotriazol-1-yloxy) tripyrrolidinophosphonium hexafluorophosphate (PyBOP), and Triphenylmethanethiol.

1. Synthesis of Thioacid Amino Acid

Boc-Phe-STrt (1)

In an eggplant flask were placed Boc-Phe-OH (165.4 mg, 0.62 mmol), PyBOP (1622.1 mg, 3.12 mmol), and Trt-SH (861.6 mg, 3.12 mmol), and this was dried under reduced pressure. After drying, DCM (3.1 ml) was added, and this was cooled to −20° C. At −20° C., DIPEA (543.0 µl) was added, and this was stirred under argon atmosphere for 2 hours. Acetic acid (543.0 µl) was then added for neutralization, and then the reaction solution was concentrated. The concentrated residue was purified on a silica gel column (elution solvent: ethyl acetate:hexane=1:10) to obtain Boc-Phe-STrt 1 (268.4 mg, 0.51 mmol, 82.2%).

$^1$H NMR (400 MHz, CDCl$_3$) δ 4.82 (d, 1H), 4.62 (q, 1H), 2.99 (q, 1H), 2.91 (m, 1H), 1.43 (s, 9H)

$^{13}$C NMR (100 MHz, CDCl$_3$) δ 197.7 HRMS (ESI): calcd for C$_{33}$H$_{33}$NO$_3$S [M+Na]$^+$ 546.2073, found 546.2076

H-Phe-SH (2)

To Boc-Phe-STrt 1 (268.4 mg, 0.51 mmol) was added 5% TIPS/TFA (5.1 ml), and this was stirred at room temperature. After 10 minutes, the reaction solution was concentrated, and to the concentrated residue was added diethyl ether (40 mL) to precipitate the target substance. The precipitated target substance was collected by centrifugation process. To the collected precipitate was added diethyl ether, and the centrifugation process was performed again to wash the precipitate. This wash was repeated twice. The precipitate was dried at ordinary temperature and pressure, and then dissolved in 0.1% TFA/H$_2$O:MeCN=1:1 and lyophilized to obtain Boc-Phe-SH 2 (91.2 mg, 0.50 mmol, 98%).

$^1$H NMR (400 MHz, DMSO) δ 7.73 (s, 2.5H), 7.26 (m, 5H), 3.68 (q, 1H), 3.35 (q, 1H), 2.92 (q, 1H)

$^{13}$C NMR (100 MHz, DMSO): δ 208.4, 137.4, 129.9, 128.8, 127.0, 63.9, 38.6

HRMS (ESI): calcd for C$_9$H$_{10}$NOS [M−H]$^-$ 180.0489, found 180.0489.

Boc-Gly-STrt (3)

In an eggplant flask were placed Boc-Gly-OH (208.2 mg, 1.19 mmol), WSCI.HCl (273.4 mg, 1.43 mmol), Trt-SH (361.3 mg, 1.31 mmol), and DMAP (14.5 mg, 0.12 mmol), and this was dried under reduced pressure. After drying, THF (5.9 ml) was added, and this was stirred under argon atmosphere for 16 hours at room temperature. Ethyl acetate (20 mL) was then added, the reaction solution was diluted, the organic phase was washed twice with each of water, saturated aqueous ammonium chloride solution, saturated aqueous sodium hydrogen carbonate solution, and saturated saline, and finally the organic phase was dried on magnesium sulfate. Magnesium sulfate was removed by filtration, and then the organic phase was concentrated. The residue was purified on a silica gel column (elution solvent: ethyl acetate:hexane=1:10) to obtain Boc-Gly-STrt 3 (304.6 mg, 0.70 mmol, 59.1%).

¹³C NMR (100 MHz, CDCl₃) δ 194.8
HRMS (ESI): calcd for $C_{26}H_{27}NO_3S$ [M+Na]⁺ 456.1604, found 456.1601.

H-Gly-SH (4)

With a procedure similar to the synthesis of H-Phe-SH 2, from raw material Boc-Gly-STrt 3 (304.6 mg, 0.70 mmol) was obtained H-Gly-SH 4 (63.1 mg, 0.69 mmol, quant).

HRMS (ESI): calcd for $C_2H_4NOS$ [M–H]⁻ 90.0019, found 90.0019.

Boc-Ala-STrt (5)

With a procedure similar to the synthesis of Boc-Phe-STrt 1, from raw material Boc-Ala-OH (633.4 mg, 3.35 mmol) was obtained Boc-Ala-STrt 5 (1243.1 mg, 2.78 mmol, 83.0%).

¹³C NMR (100 MHz, CDCl₃) δ 198.6
HRMS (ESI): calcd for $C_{27}H_{29}NO_3S$ [M+Na]⁺ 470.1760, found 470.1766.

H-Ala-SH (6)

With a procedure similar to the synthesis of H-Phe-SH 2, from raw material Boc-Ala-STrt 5 (1243.1 mg, 2.78 mmol) was obtained H-Ala-SH 6(277.7 mg, 2.64 mmol, 95%).

¹H NMR (400 MHz, DMSO) δ 7.69 (s, 3H), 3.49 (q, 1H), 1.32 (d, 3H)
¹³C NMR (100 MHz, DMSO) δ 210.0, 58.4, 19.0
HRMS (ESI): calcd for $C_2H_6NOS$ [M–H] 104.0176, found 104.0176.

Boc-Ser(tBu)-STrt (7)

With a procedure similar to the synthesis of Boc-Phe-STrt 1, from raw material Boc-Ser(tBu)-OH.DCHA (717.6 mg, 1.62 mmol) was obtained Boc-Ser(tBu)-STrt 7 (685.2 mg, 1.48 mmol, 91.1%).

¹H NMR (400 MHz, CDCl₃) δ 5.44 (d, 1H), 4.33 (d, 1H), 3.76 (dd, 1H), 3.43 (dd, 1H), 1.45 (s, 9H)
¹³C NMR (100 MHz, CDCl₃) δ 197.9

H-Ser-SH (8)

With a procedure similar to the synthesis of H-Phe-SH 2, from raw material Boc-Ser(tBu)-STrt 7 (685.2 mg, 1.48 mmol) was obtained H-Ser-SH 8 (173.3 mg, 1.43 mmol, 97%).

¹H NMR (400 MHz, DMSO) δ 7.69 (s, 3H), 5.11 (s, 1H), 3.96 (q, 1H), 3.52 (m, 2H)
¹³C NMR (100 MHz, DMSO) δ 206.5, 65.0, 62.5
HRMS (ESI): calcd for $C_3H_6NO_2S$ [M–H]⁻ 120.0125, found 120.0125.

2. Homoolygomerization Reaction of Thioacid Amino Acid

Polymerization of H-Phe-SH

Figure 1:
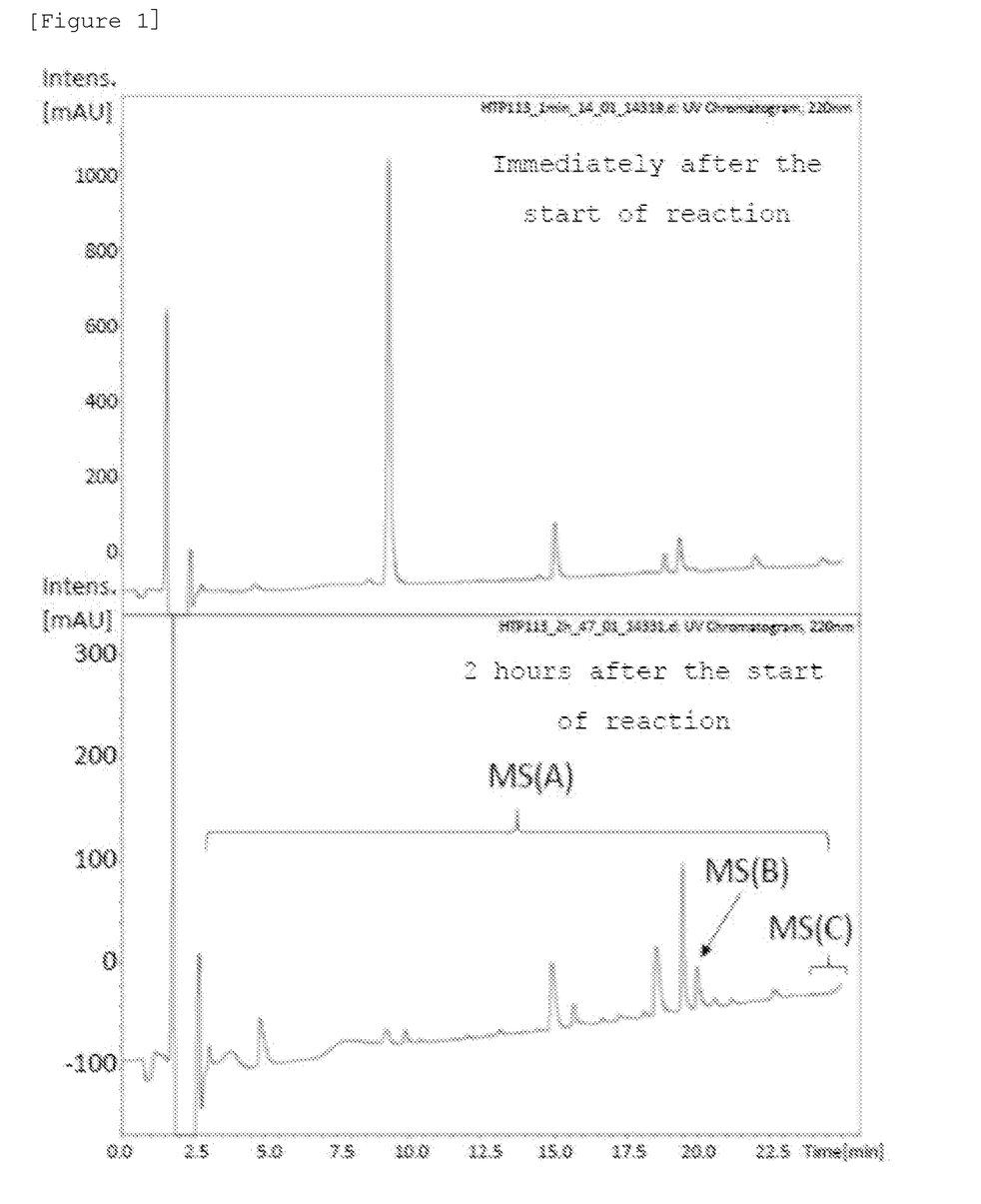
FIG. 1 shows the LC-MS results of the product at immediately after and two hours after the oxidation reaction of H-Phe-SH.

To H-Phe-SH 2 (0.40 mg, 2.2 μmol) dissolved in water (221 μl) was added iron chloride (III) FeCl₃ (2.98 mg, 11.0 μmol) dissolved in water (5 μL), and this was left still at room temperature (pH=1.26). At 0 hour and 2 hours after the start of reaction, 2 μL of each solution was measured out with a Pipetman, the reaction was stopped with phosphate buffer at pH 7 (20 μL), and analysis was performed by LC-MS. FIG. 1 shows the result of after 2 hours (wavelength 220 nm) (LC-MS analysis method: C18 5 μm, 4.6×100 mm, 0.1% FA:0.1% FA in 90% MeCN=95:5 to 45:55, 20 minutes, flow rate at 0.2 ml/minutes).

Figure 2:
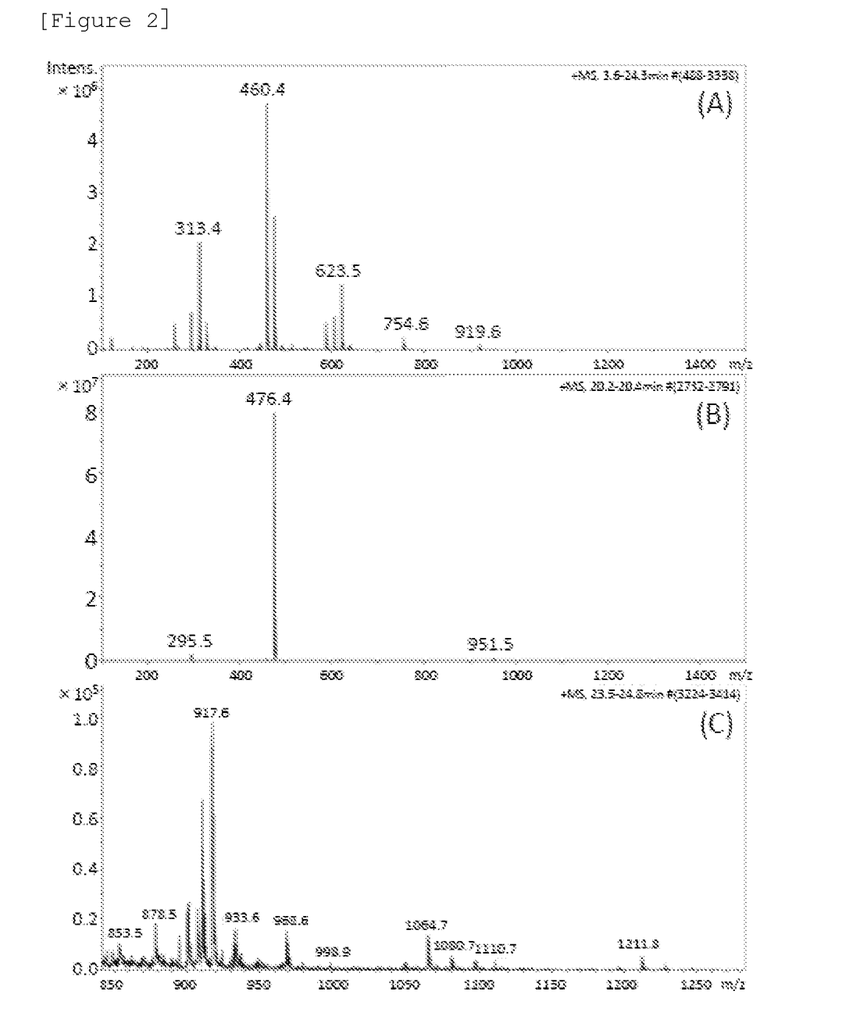
FIG. 2 shows the mass spectrometry results of the fractions corresponding to MS(A), MS(B), and MS(C) in FIG. 1.

FIG. 2 is the result of mass spectrometry of each of the ranges MS(A), MS(B), and MS(C) in FIG. 1. m/z and composition of MS(A), MS(B), and MS (C) were each as shown below: (A) m/z=460.4:H—FFF—OH, (B) m/z=476.4:H—FFF—SH, (C) m/z=1211.8:H—FFFFFFFF—SH.

3. Heteroolygomerization Reaction of Thioacid Amino Acid

Oligomerization of H-Phe-SH and H-Ala-SH

Figure 3:
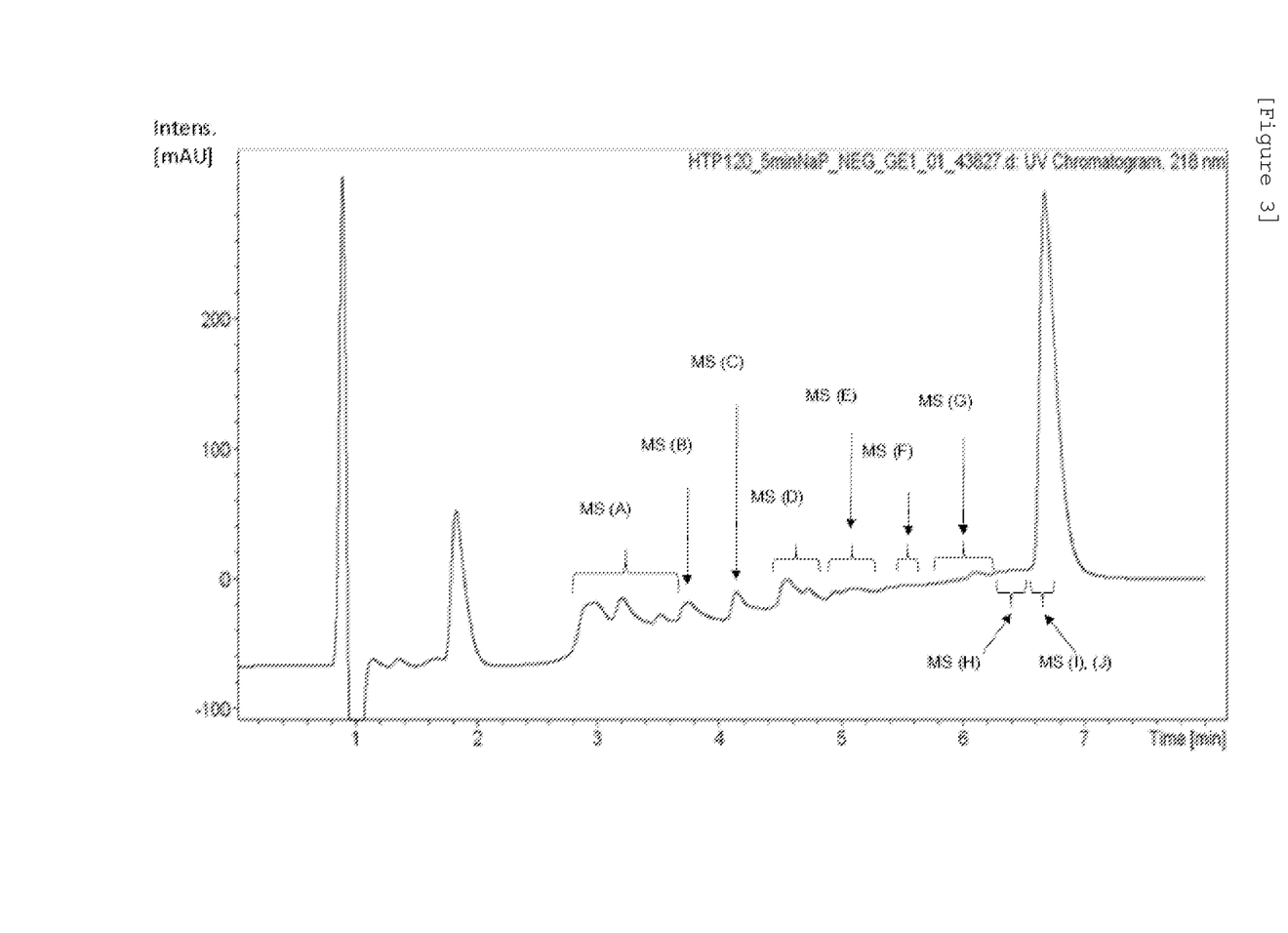
FIG. 3 shows the UHPLC result at one minute after the oligomerization reaction of H-Phe-SH and H-Ala-SH.

To a mixture of H-Phe-SH 2 (0.7 mg, 3.9 μmol) and H-Ala-SH 6 (1.0 mg, 9.5 μmol) dissolved in water (520 μl) was added iron chloride (III) FeCl₃ (5.2 mg, 19.2 μmol) dissolved in water (5 μL), and this was left still at room temperature (pH=1.40). At 5 minutes after the start of reaction, 2 μL of solution was measured out with a Pipetman, the reaction was stopped with phosphate buffer at pH 7 (20 μL), and analysis was performed with UHPLC. FIG. 3 shows the result of after 1 minute (wavelength 218 nm) (UHPLC analysis method: C18 5 μm, 4.6×50 mm, 0.1% FA:0.09% FA in 90% MeCN=95:5 to 5:95, 5 minutes, flow rate at 0.2 ml/minutes).

Figure 4:
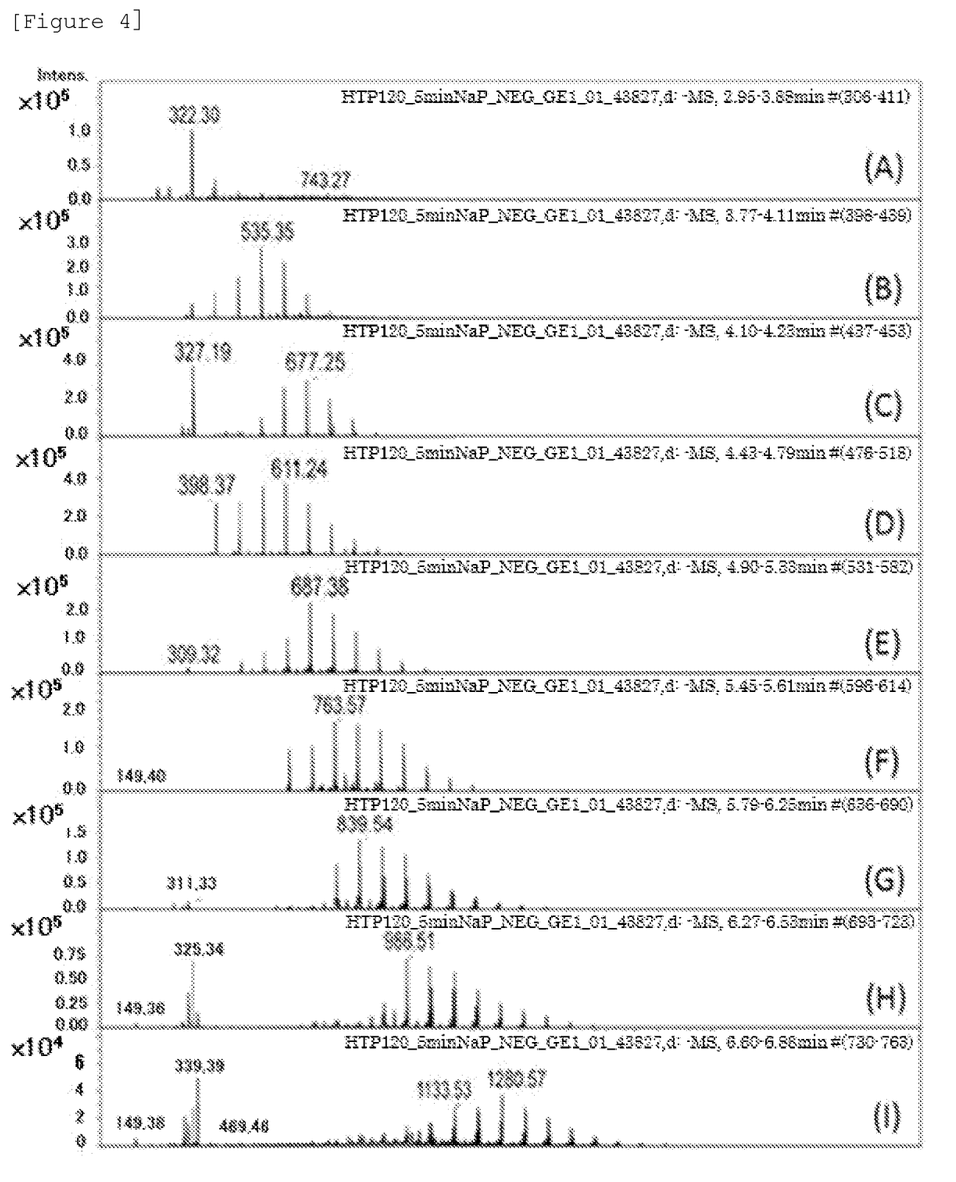
FIG. 4 shows the mass spectrometry results measured for fractions (A) to (I). Fractions (A) to (I) correspond to MS(A) to MS(I) in FIG. 3, respectively.
Figure 5:
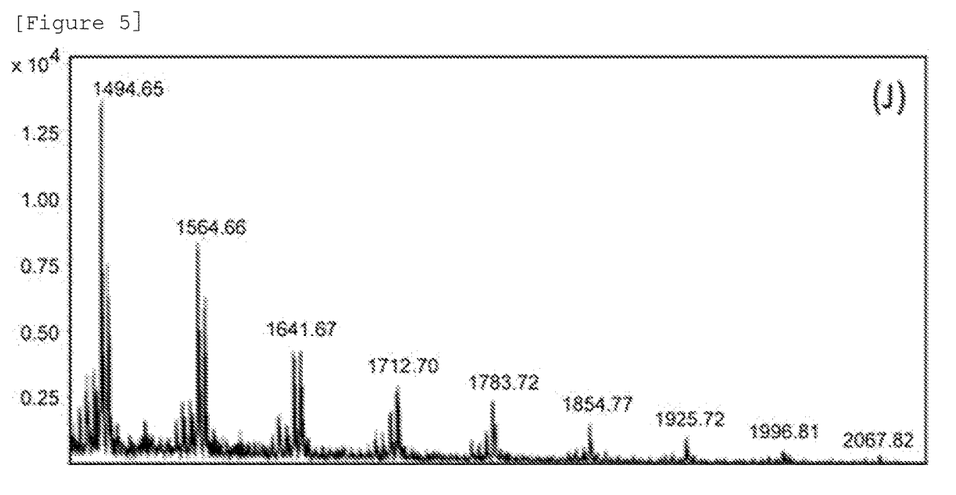
FIG. 5 shows the mass spectrometry result measured for fraction (J). Fraction (J) corresponds to MS(J) in FIG. 3.
Figure 6:
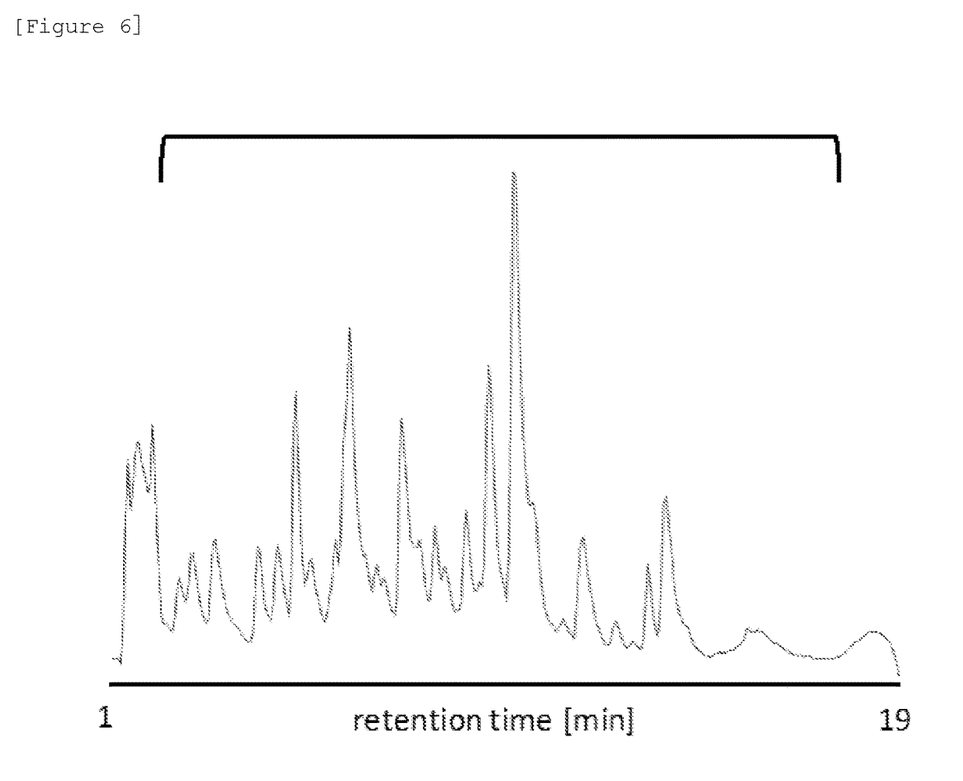
FIG. 6 shows the TIC chromatogram of analytical LC-MS of the oligomerization reaction of Phe-SH and Lys-SH.
Figure 7:
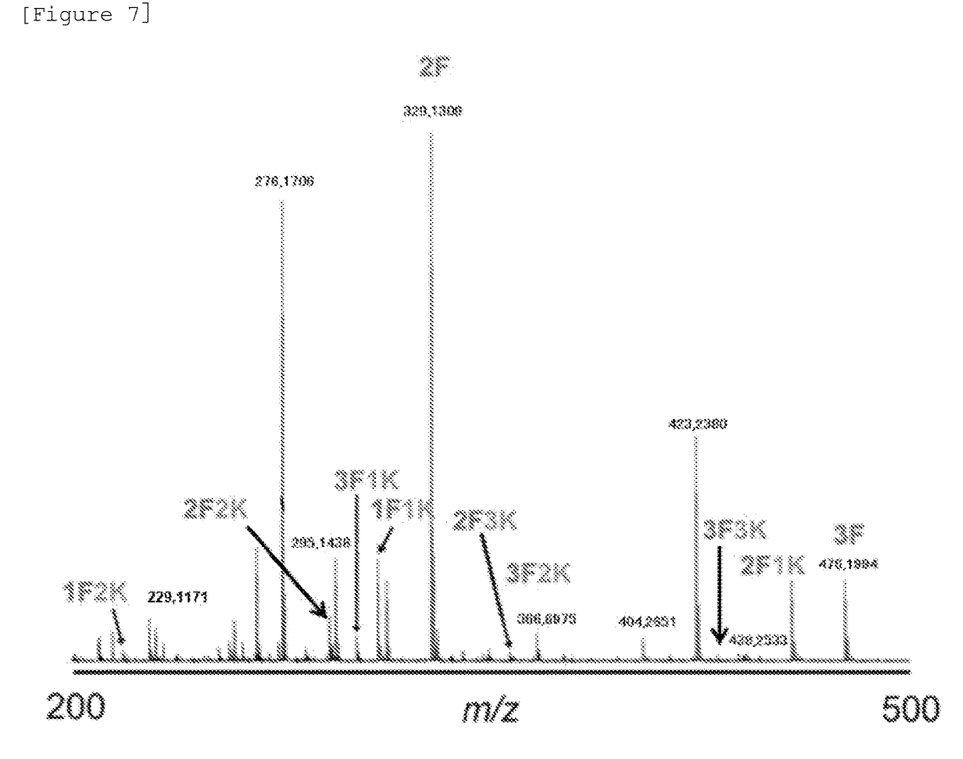
FIG. 7 shows the integrated MS spectrum obtained from the TIC chromatogram in FIG. 6 in the range of 2.2-14.0 min.
Figure 8:
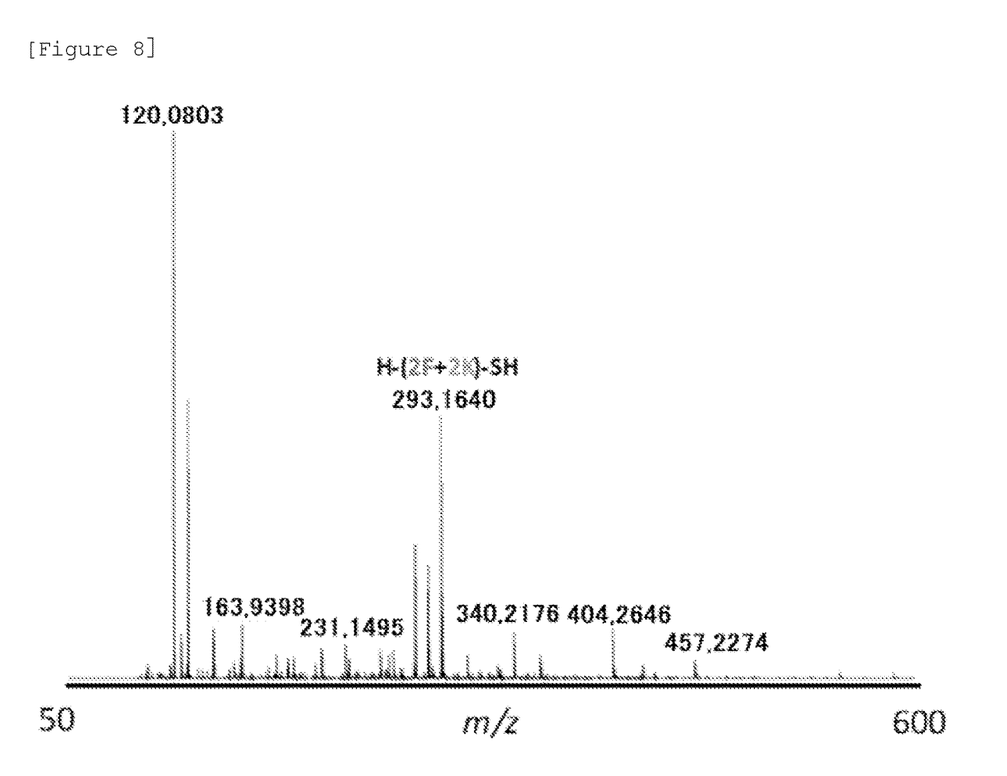
FIG. 8 shows the MS spectrum of 2F2K oligopeptide obtained from the peak top at 7 min. in the TIC chromatogram of FIG. 6. HRMS (ESI): calcd for $C_{30}H_{40}N_6O_4S$ $[M+2H]^{2+}$ 293.1645, found 293.1640.
Figure 9:
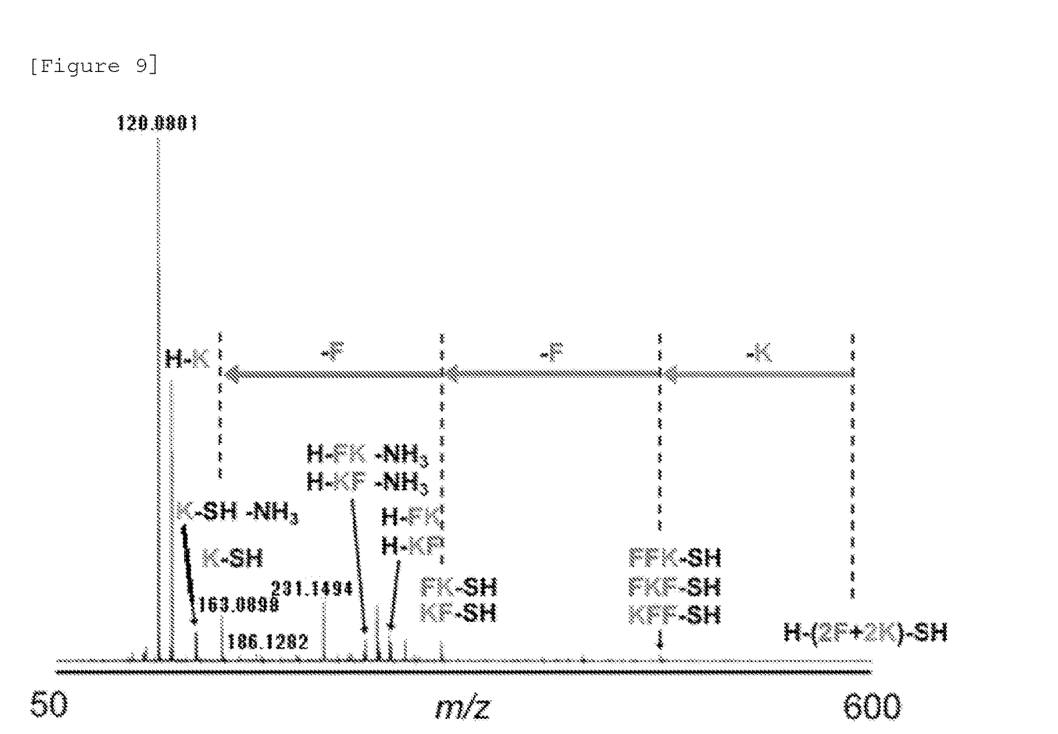
FIG. 9 shows the CID fragmentation pattern of 2F2K oligopeptide.

FIG. 4 and FIG. 5 show the compositions of principal products observed by the single-letter expressions of F=Phe and A=Ala. (A) to (J) in FIGS. 4 and 5 each correspond to the mass spectrometry results measured for the fractions shown with MS(A) to MS(J) in FIG. 3. FIG. 5(J) is a partial magnification of FIG. 4(I). m/z and composition of MS(A) to MS(J) were each as shown below: (A) m/z=322.20:H—F1A2-OH, (B) m/z=535.35:H—F1A5-SH, (C) m/z=327.19: H—F2-SH, m/z=677.25:H—F1A7-SH, (D) m/z=398.37: H—F2A1-SH, m/z=611.24:H—F2A4-SH, (E) m/z=687.38: H—F3A3-SH, (F) m/z=763.57:H—F4A2-SH, (G) m/z=839.54:H—F5A1-SH, (H) m/z=986.51:H—F6A1-SH, (I) m/z=1133.53:H—F7A1-SH, m/z=1280.57:H—F8A1-SH, (J) m/z=2067.82:H—F9A10-SH.

The maximum peptide observed by mass spectrometry analyzed at 5 minutes after the start of reaction was composed of 19 residues of amino acids, and the composition thereof was a thioacid peptide comprising 9 residues of phenylalanine and 10 residues of alanine (FIG. 5J).

4. Oligomerization of Phe-SH and Lys-SH

Boc-Lys (Boc)-STrt (13)

With a method substantially identical to the above synthesis of Boc-Phe-STrt 1, from Boc-Lys(Boc)-OH (1.05 g, 1.98 mmol) was obtained Boc-Lys(Boc)-STrt 13 (1.10 g, 1.82 mmol, 92%) as an amorphous product.

$[\alpha]_D^{20}$-26.78 (c=0.95, CHCl₃). ¹H NMR (400 MHz, CDCl₃) δ: 7.26 (m), 4.99 (d, 1H), 4.49 (1H), 4.28 (q, 1H), 3.05 (q, 2H), 1.67 (m, 1H), 1.45 (s, 9H), 1.44 (s, 9H), 1.40 (m, 1H), 1.18 (m, 2H). ¹³C NMR (100 MHz, CDCl₃) δ: 198.2, 156.1, 155.3, 143.6, 129.9, 127.7, 127.1, 80.1, 79.2, 70.3, 60.3, 40.0, 32.2, 29.6, 28.5, 28.3, 22.2. HRMS (ESI): calcd for $C_{35}H_{44}N_2NaO_5S$ [M+Na]⁺ 627.2863, found 627.2861.

H-Lys-SH (14)

With a method substantially identical to the synthesis of H-Phe-SH 2, from Boc-Lys(Boc)-STrt 13 (840 mg, 1.33 mmol) was obtained H-Lys-SH 14 (165 mg, 1.02 mmol, 73%) as white powder. $[\alpha]_D^{20}$4.73 (c=0.74, H₂O:MeCN=1: 1). ¹H NMR (400 MHz, D₂O) δ: 3.86 (t, 1H), 2.87 (t, 2H), 1.85 (m, 2H), 1.57 (m, 2H), 1.33 (m, 2H). ¹³C NMR (100 MHz, D₂O) δ: 214.4, 62.4, 39.0, 31.4, 26.3, 21.1. HRMS (ESI): calcd for $C_6H_{13}N_2OS$[M–H]⁻ 161.0754, found 180.0755.

Oligomerization of Phe-SH and Lys-SH

H-Phe-SH 2 (0.1 mg, 0.55 μmol) and H-Lys-SH 14 (0.45 mg, 2.76 μmol) were dissolved in degassed water (47.5 μL). To this solution was added FeCl₃.6H₂O solution (0.1 mg/μL, 7.5 μL) comprising 5-folds excess of FeCl₃.6H₂O (2.76 μmol). At each timepoint of reaction, the reaction of a portion of the reaction mixture was stopped with phosphate buffer (pH 7), LCMS analysis was performed, and the progress of the reaction was monitored (Table 1, FIGS. 6-9). All LC-MS analysis were performed at 5 minutes after the reaction was stopped.

TABLE 1

Table. HRMS of oligopeptides observed in the oligomerization reaction of Phe-SH and Lys -SH

| FK peptide | Ion Charge | Calculated M5 | Observed M5 | Error (ppm) |
|---|---|---|---|---|
| 1F + 1K | [M + H]$^+$ | 310.1584 | 310.1581 | −1.0 |
| 1F + 2K | [M + 2H]$^{2+}$ | 219.6303 | 219.6302 | −0.5 |
| 1F + 3K | [M + 2H]$^{2+}$ | 283.6778 | 283.6774 | −1.5 |
| 1F + 4K | [M + 2H]$^{2+}$ | 347.7253 | 347.7242 | −3.5 |
| 2F + 1K | [M + H]$^+$ | 457.2255 | 457.2259 | −1.9 |
| 2F + 2K | [M + 2H]$^{2+}$ | 293.1645 | 293. 1644 | −0.2 |
| 2F + 3K | [M + 2H]$^{2+}$ | 357.2120 | 357.2122 | 0.6 |
| 2F + 4K | [M + 2H]$^{2+}$ | 421.2595 | 421.2595 | 0.1 |
| 2F + 5K | [M + 3H]$^{3+}$ | 323.8737 | 323.8737 | −0.1 |
| 2F + 6K | [M + 3H]$^{3+}$ | 366.5721 | 355.5719 | −0.4 |
| 3F + 1K | [M + H]$^+$ | 504.2952 | 604.2958 | 0.9 |
| 3F + 2K | [M + 2H]$^{2+}$ | 366.6957 | 366.6979 | −2.3 |
| 3F + 3K | [M + 2H]$^{2+}$ | 430.7462 | 430.7462 | 0 |
| 3F + 4K | [M + 3H]$^{3+}$ | 330.1982 | 330.1983 | 0.2 |
| 3F + 5K | [M + 3H]$^{3+}$ | 372.8965 | 372.8965 | 0 |
| 3F + 6K | [M + 4H]$^{4+}$ | 415.5949 | 415.5953 | 1.1 |
| 3F + 7K | [M + 4H]$^{4+}$ | 343.9717 | 343.9718 | 0.4 |
| 3F + 8K | [M + 4H]$^{4+}$ | 375.9954 | 375.9950 | −1.1 |
| 4F + 1K | [M + H]$^+$ | 374.1854 | 374.852 | −0.7 |
| 4F + 2K | [M + 2H]$^{2+}$ | 440.2329 | 440.2330 | 0.1 |
| 4F + 3K | [M + 2H]$^{2+}$ | 335.5227 | 335.5226 | −0.2 |
| 4F + 4K | [M + 3H]$^{3+}$ | 379.2210 | 379.2209 | −0.4 |
| 4F + 5K | [M + 3H]$^{3+}$ | 421.9193 | 421.9194 | 0.1 |
| 4F + 6K | [M + 4H]$^{4+}$ | 348.7151 | 348.7123 | −7.9 |
| 4F + 7K | [M + 4H]$^{4+}$ | 380.7388 | 380.7390 | 0.6 |
| 4F + 8K | [M + 4H]$^{4+}$ | 412.7625 | 412.7610 | −3.7 |
| 5F + 1K | [M + 2H]$^{2+}$ | 449.7197 | 449.7198 | 0.3 |
| 5F + 2K | [M + 2H]$^{2+}$ | 513.7671 | 513.7665 | −0.5 |
| 5F + 3K | [M + 3H]$^{3+}$ | 385.5455 | 385.5458 | 0.8 |
| 5F + 4K | [M + 3H]$^{3+}$ | 428.2438 | 428.2440 | 0.3 |
| 5F + 4K | [M + 4H]$^{4+}$ | 353.4584 | 353.4582 | −0.6 |
| 5F + 5K | [M + 4H]$^{4+}$ | 385.4822 | 385.4823 | 0.5 |
| 5F + 6K | [M + 4H]$^{4+}$ | 471.5059 | 471.5065 | 1.5 |
| 5F + 7K | [M + 5H]$^{5+}$ | 359.8252 | 359.8248 | −1.0 |
| 6F + 1K | [M + 2H]$^{2+}$ | 523.2539 | 523.2539 | 0 |

The invention claimed is:

1. A method for manufacturing a polymer of amino acids linked by peptide bonds, the method comprising:
   (A) a step of preparing first and second amino acid derivatives each independently having a structure of Compound Formula (1):

$$H_2N—CH(R)—COSH \qquad (1),$$

wherein R represents the side chain of any amino acid optionally comprising a protecting group; and
   (B) a step of subjecting said first amino acid derivative and said second amino acid derivative to an oxidation reaction to obtain a compound of Compound Formula (2):

$$H_2N—CH(R)—CO—HN—CH(R)—CO—SH \qquad (2),$$

wherein each R independently represents the side chain of any amino acid; and
   wherein at least one of said first amino acid derivative and second amino acid derivative does not possess a protecting group.

2. The manufacturing method according to claim 1, wherein said first amino acid derivative and second amino acid derivative both do not possess a protecting group.

3. The manufacturing method according to claim 1, further comprising:
   (C) a step of subjecting the compound of Compound Formula (2) obtained in step (B) to an oxidation reaction with a third amino acid derivative
   having a structure of Compound Formula (1), wherein R is as defined in Compound Formula (1),
   to obtain a compound of Compound Formula (3):

$$H_2N—CH(R)—CO—(HN—CH(R)—CO)_2—SH \qquad (3),$$

wherein each R independently represents the side chain of any amino acid.

4. The manufacturing method according to claim 3, wherein step (C) is repeated multiple times to obtain a compound of Compound Formula (4):

$$H_2N—CH(R)—CO—(HN—CH(R)—CO)_n—SH \qquad (4),$$

wherein each R independently represents the side chain of any amino acid, and n represents an integer that is 2 or more.

5. The manufacturing method according to claim 3, wherein said third amino acid derivative does not possess a protecting group.

6. The manufacturing method according to claim 1, further comprising:
   (D) a step of reacting the compound of Compound Formula (2) obtained in step (B) with a nucleophilicity reagent of Compound Formula (5):

$$H—X \qquad (5),$$

wherein X represents a substituent bound by an atom selected from the group consisting of N, O, S, and Se,
   to obtain a compound of Compound Formula (6):

$$H_2N—CH(R)—CO—(HN—CH(R)—CO)_m—X \qquad (6),$$

wherein each R independently represents the side chain of any amino acid, m represents any integer, and X represents a substituent bound by an atom selected from the group consisting of N, O, S, and Se.

7. The manufacturing method according to claim 6, wherein X is a substituent bound by an N atom or S atom.

8. The manufacturing method according to claim 4, wherein the method provides a polymer comprising 4 to 20 amino acids.

9. The manufacturing method according to claim 1, wherein the side chain of the first or second amino acid derivative is an unprotected 4-aminobutyl group.

10. The manufacturing method according to claim 1, wherein the side chains of said first and second amino acid derivatives are identical.

11. The manufacturing method according to claim 10, wherein said side chains are all methyl groups.

12. A method for manufacturing a polymer of two or more amino acids linked by a peptide bond, the method comprising:
   (a) a step of preparing two or more amino acid derivatives having a structure of Compound Formula (1):

$$H_2N—CH(R)—COSH \qquad (1),$$

wherein R represents the side chain of any amino acid optionally comprising a protecting group; and
   (b) a step of subjecting said two or more amino acid derivatives to an oxidation reaction to obtain more than one compound of Compound Formula (7):

$$H_2N—CH(R)—CO—(HN—CH(R)—CO)_x—SH \qquad (7),$$

wherein each R independently represents the side chain of any amino acid, and x represents any integer,
   and/or Compound Formula (8):

$$H_2N—CH(R)—CO—(HN—CH(R)—CO)_y—S—S—(CO—CH(R)—NH)_zCO—CH(R)—NH_2 \qquad (8),$$

wherein each R independently represents the side chain of any amino acid, and y and z represent any integer, wherein a portion or all of said two or more amino acid derivatives do not possess a protecting group.

13. The method according to claim 12, wherein all of said two or more amino acid derivatives do not possess a protecting group.

14. The method according to claim 12, wherein the compound obtained in step (b) comprises the compound of Compound Formula (7).

15. The manufacturing method according to claim 14, further comprising:

(c1) a step of reacting the compound of Compound Formula (7) obtained in step (b) with a nucleophilicity reagent of Compound Formula (5):

$$H-X \tag{5},$$

wherein X represents a substituent bound by an atom selected from the group consisting of N, O, S, and Se, to obtain a compound of Compound Formula (9):

$$H_2N-CH(R)-CO-(HN-CH(R)-CO)_x-X \tag{9}$$

wherein each R independently represents the side chain of any amino acid, x represents any integer, and X represents a substituent bound by an atom selected from the group consisting of N, O, S, and Se.

16. The manufacturing method according to claim 15, wherein X is a substituent bound by an N atom or S atom.

17. The manufacturing method according to claim 12, wherein the compound obtained in step (b) comprises the compound of Compound Formula (8).

18. The manufacturing method according to claim 17, further comprising:

(c2) a step of reacting the compound of Compound Formula (8) obtained in step (b) with a nucleophilicity reagent of Compound Formula (5):

$$H-X \tag{5},$$

wherein X represents a substituent bound by an atom selected from the group consisting of N, O, S, and Se, to obtain a compound of Compound Formula (10):

$$H_2N-CH(R)-CO-(HN-CH(R)-CO)_y-X \tag{10},$$

wherein each R independently represents the side chain of any amino acid, y represents any integer, and X represents a substituent bound by an atom selected from the group consisting of N, O, S, and Se, and Compound Formula (11):

$$H_2N-CH(R)-CO-(HN-CH(R)-CO)_z-X \tag{11},$$

wherein each R independently represents the side chain of any amino acid, z represents any integer, and X represents a substituent bound by an atom selected from the group consisting of N, O, S, and Se.

19. The manufacturing method according to claim 18, wherein X is a substituent bound by an N atom or S atom.

20. The manufacturing method according to claim 12, wherein the method provides a polymer comprising 4 to 20 amino acids.

21. The manufacturing method according to claim 12, wherein at least one side chain of said two or more amino acid derivatives is an unprotected 4-aminobutyl group.

22. The manufacturing method according to claim 12, wherein the side chains of said two or more amino acid derivatives are identical.

23. The manufacturing method according to claim 22, wherein said side chains are all methyl groups.

24. The manufacturing method according to claim 12, wherein the method produces a polypeptide library.

\* \* \* \* \*

UNITED STATES PATENT AND TRADEMARK OFFICE
CERTIFICATE OF CORRECTION

PATENT NO. : 11,214,592 B2
APPLICATION NO. : 16/489950
DATED : January 4, 2022
INVENTOR(S) : Kajihara et al.

It is certified that error appears in the above-identified patent and that said Letters Patent is hereby corrected as shown below:

In the Specification

Column 14, Line 53: Please correct "WSCI.HCl" to read -- WSCI·HCl --

Column 15, Line 30: Please correct "OH.DCHA" to read -- OH·DCHA --

Column 16, Line 65: Please correct "FeCl$_3$.6H$_2$O" to read -- FeCl$_3$·6H$_2$O --

Column 16, Line 66: Please correct "FeCl$_3$.6H$_2$O" to read -- FeCl$_3$·6H$_2$O --

Signed and Sealed this
Ninth Day of August, 2022

Katherine Kelly Vidal
*Director of the United States Patent and Trademark Office*